US006218186B1

(12) United States Patent
Choi et al.

(10) Patent No.: US 6,218,186 B1
(45) Date of Patent: Apr. 17, 2001

(54) HIV-MSCV HYBRID VIRAL VECTOR FOR GENE TRANSFER

(75) Inventors: John Kim Choi, Boothwyn; Alan M. Gewirtz, Narberth, both of PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/439,000

(22) Filed: Nov. 12, 1999

(51) Int. Cl.[7] ............................. C12N 15/86; C12N 15/09; C12N 15/63; C07H 21/04; C12P 19/34

(52) U.S. Cl. ..................... 435/456; 435/320.1; 435/455; 435/91.33; 536/23.1; 536/24.1; 536/24.2

(58) Field of Search ..................... 424/93.1; 435/91.33, 435/320.1, 455, 456; 514/44; 536/23.1, 24.1–24.2

(56) References Cited

U.S. PATENT DOCUMENTS

| | | | |
|---|---|---|---|
| 4,650,764 | 3/1987 | Temin et al. ...................... | 435/325 |
| 5,686,279 | 11/1997 | Finer et al. ...................... | 435/456 |
| 5,834,256 | 11/1998 | Finer et al. ...................... | 435/91.33 |
| 5,858,740 | 1/1999 | Finer et al. ...................... | 435/456 |

OTHER PUBLICATIONS

Eck, S.L., and Wilson, J.M. Gene–based therapy, Goodman & Gilman's The pharmacological basis of therapeutics, Ninth edition, pp. 77–101, 1996.*

Federico, M. Lentiviruses as gene delivery vectors, Current Opinion in Biotechnology 10:448–453, 1999.*

Miller, A.D. Development and applications of retroviral vectors, Retroviruses (Coffin J.M., Hughes S.H., and Varmus, H.E., eds.) pp. 437–473, 1997.*

Parolin, C. et al. Use of cis–and trans–Acting viral regulatory sequences to improve expression of human immunodeficiency virus vectors in human lymphocytes, Virology 222:415–422, 1996.*

Barillari et al., "Inflammatory Cytokines Synergize with the HIV–1 Tat Protein to Promote Angiogenesis and Kaposi's Sarcoma Via Induction of Basic Fibroblast Growth Factor and the $\alpha_v\beta_3$ Integrin[1]", 1999 Journal of Immunology 163(4)1929–35.

Blömer et al., "Highly Efficient and Sustained Gene Transfer in Adult Neurons with a Lentivirus Vector", 1997 Journal of Virology 71(9) p. 6641–9.

Bukrinsky et al., "A nuclear localization signal within HIV–1 matrix protein that governs infection of non–dividing cells", 1993 Nature 365 (6447) p. 666–9.

Case et al., "Stable transduction of quiescent CD34+CD38− human hematopoietic cells by HIV–1–based lentiviral vectors", 1999 Proc. Natl. Acad. Sci. USA 96(6); 2988–93.

Chirivi et al., "Human Immunodeficiency Virus–1 (HIV–1)–Tat Protein Promotes Migration of Acquired Immunodeficiency Syndrome–Related Lymphoma Cells and Enhances Their Adhesion to Endothelial Cells", 1999 Blood; 94(5) 1747–54.

Connor et al., "Vpr Is Required for Efficient Replication of Human Immunodeficiency Virus Type–1 in Mononuclear Phagocytes", 1995 Virology 206(2): 935–44.

Demarchi et al., "Human Immunodeficiency Virus Type 1 Tat Protein Activates Transcription Factor NF-$_k$B through the Cellular Interferon–Inducible, Double–Standard RNA–Dependent Protein Kinase, PKR", 1999 Journal of Virology 73(8); 7080–6.

Dinauer et al., "Long–Term Correction of Phagocyte NADPH Oxidase Activity by Retroviral–Mediated Gene Transfer in Murine X–Linked Chronic Granulomatous Disease", 1999 Blood, 94(3); 914–22.

Evans, et al., "Human Cord Blood $CD34^+CD38^{31}$ Cell Transduction via Lentivirus–Based Gene Transfer Vectors", 1999 Human Gene Therapy 10:1479–1489.

Frazier et al., "Retrovirus–Mediated Transfer and Long–Term Expression of HIV Type 1 tat Gene in Murine Hematopoietic Tissues", 1994 Aids Research and Human Retroviruses 10; 1517–1524.

Gothot et al., "Cell Cycle–Related Changes in Repopulating Capacity of Human Mobilized Peripheral Blood $CD34^+$ Cells in Non–Obese Diabetic/Severe Combined Immune–Deficient Mice", 1998 Blood 92; 8; 2641–2649.

Hawley, et al., "Thrombopoietic potential and serial repopulating ability of murine hematopoietic stem cells constitutively expressing interleukin 11", 1996 Proc. Natl. Acad. Sci. USA 93; 10297–10302.

Hawley et al., "Versatile retroviral vectors for potential use in gene therapy", 1994 Gene Therapy 1; 136–138.

Kafri, et al., "Sustained expression of genes delivered directly into liver and muscle by lentiviral vectors", 1997 Nature Genetics 17; 314–317.

Kohn et al., "T lymphocytes with a normal ADA gene accumulate after transplantation of transduced autologous umbilical cord blood $CD34^+$ cells in ADA–deficient SCID neonates", 1998 Nature Medicine 4: 775–780.

Kohn et al., "Engraftment of gene–modified umbilical cord blood cells in neonates with adenosine deaminase deficiency", 1995 Nature Medicine 1; 1017–1023.

(List continued on next page.)

Primary Examiner—Deborah Crouch
Assistant Examiner—Quang Nguyen
(74) Attorney, Agent, or Firm—Licata & Tyrrell P.C.

(57) ABSTRACT

A hybrid viral vector for transfer of selected genes to cells and mammals is provided. The vector is a hybrid of human immunodeficiency-based lentivirus and murine stem cell retrovirus.

3 Claims, 1 Drawing Sheet

OTHER PUBLICATIONS

Knaän–Shanzer et al., Cell cycle state, response to hemopoietic growth factors and retroviral vector–mediated transduction of human hemopoietic stem cells, 1995 *Gene Therapy* 3; 323–333.

Lefevre et al., "Cutting Edge:HIV–1 Tat Protein Differentially Modulates the B Cell Response of Naive, Memory, and Germinal Center B Cells[1]", 1999 *Journal of Immunology* 163(3) 1119–22.

Maggirwar et al., "HIV–1 Tat–Mediated Activation of Glycogen Synthse Kinase–3β Contributes to Tat–Mediated Neurotoxicity", 1999 *Journal of Neurchemistry* 73(2);578–86.

Miller et al., "Gene Transfer by Retrovirous Vectors Occurs Only in Cells That Are Actively Replicating at the Time of Infection", 1990 *Molecular & Cellular Biology* 10(8); 4239–42.

Miyoshi et al., "Transduction of Human $CD34^+$ Cells That Mediate Long–Term Engraftment of NOD/SCID Mice by HIV Vectors", 1999 *Science* 283(5402); 682–6.

Naldini et al., "Efficient transfer, integration, a nd sustained long–term expression of the transgene in adult rat brains injected with a lentiviral vector", 1996 *Pro. Natl. Sci. USA* 93(21); 11382–8.

Pear et al., "Efficient and Rapid Induction of a Chronic Myelogenous Leukemia–Like Myeloproliferative Disease in Mice Receiving P210 ber/abl–Transduced Bone Marrow", 1998 *Blood* 92(10); 3780–92.

Persons et al., Retroviral–Mediated Transfer of the Green Fluorescent Protein Gene Into Murine Hematopoictic Cells Facilitates Scoring and Selection of Transduced Progenitors in Vitro and Identificiation of Genetically Modified Cells In Vivo, 1997 *Blood* 90(5); 1777–1786.

Schwartz et al., "In Vivo Protein Transduction: Delivery of a Biologically Active Protein into the Mouse", 1999 *Science* 285; 1569–1572.

Sutton et al., "Human Immunodeficiency Virus Type 1 Vectors Efficiently Transduce Human Hematopoietic Stem Cells", 1998 *Journal of Virology* 72(7); 5781–5788.

Uchida et al., "HIV, but not murine leukemia virus, vectors mediate high efficiency gene transfer into freshly isolated $G_0/G_1$ human hematopoietic", 1998 *Proc. Natl. Acad. Sci. USA* 95; 11939–11944.

Verma et al., "Gene therapy–promises, problems and prospects", 1997 *Nature* 389; 239–242.

Weiss et al., "HIV–1 Tat Induces Monocyte Chemoattractant Protein–1–Mediated Monocyte Transmigration Across a Model of the Human Blood–Brain barrier and Up–Regulates CCR5 Expression on Human Monocytes[1]", 1999 *Journal of Immunology* 163(5); 2953–9.

Zufferey et al., "Multiply attenuated lentiviral vector achieves efficient gene delivery in vivo", 1997 *Nature* 15; 871–874.

Barette et al., "Increased Pit–2 mRNA Levels and Improved Amphotropic Retrovirus Mediated Gene Transfer Into Mouse Hematopoietic Stem Cells After 6 Days In–Vitro Culture in IL–3, IL–6 and SCF", 1998 *Blood Journal of the American Society of Hematology* 91(10) 468a.

\* cited by examiner

HIV-MSCV HYBRID VIRAL VECTOR FOR GENE TRANSFER

INTRODUCTION

This invention was supported in part by funds from the U.S. government (NIH Grant Nos. KO8 CA75330-01 and PO1 DK52558-01A1) and the U.S. government may therefore have certain rights in the invention.

BACKGROUND OF THE INVENTION

The hematopoietic stem cell (HSC) is an ideal target cell for gene therapy because a single modified cell can potentially regenerate the entire hematopoietic system in which every cell contains the modification. While murine HSC can be transduced using retroviral vectors based on murine leukemic viruses (MuLV), human HSC resist such manipulation (Dinauer, M. C. et al. 1999. Blood 94:914–922; Persons, D. A. et al. 1997. Blood 90:1777–1786; Hawley, R. G. et al. 1996. Proc. Natl. Acad. Sci. USA 93:10297–10302).

One possible explanation is that viral integration of these vectors requires cell division (Miller, D. G. et al. 1990. Molec. Cell Biol. 10:4239–4242). In human hematopoietic stem cells that divide slowly, the virus may be neutralized within the cytoplasm before division occurs. This issue is typically addressed by optimizing culture conditions for maximal cell replication. While this strategy increases the transduction of hematopoietic progenitor cells, transduction of the human HSC remains poor (Kohn, D. B. et al. 1998. Nature Med. 4:775–780; Kohn, D. B. et al. 1995. Nature med. 1:1017–1023; Knaan-Shanzer, S. et al. 1996. Gene Therapy 3:323–333). Furthermore, ex vivo initiation of replication of the stem cells is associated with commitment, differentiation, and loss of the re-population potential (Gothot, A. et al. 1998. Blood 92:2641–2649).

The murine stem cell virus (MSCV) based retroviral vectors is another effective vehicle for delivery and expression of exogenous genes in human hematopoietic progenitor cells. Again, a major limitation of this MULV-based vector, however, is that viral integration requires cell division.

These findings suggest that a vector that is less dependent on replication would be better at transducing human HSC.

Unlike the MuLV, the human immunodeficiency virus (HIV) can integrate into the genome of non-dividing cells. The HIV virus encodes a gag core protein with a nuclear localization signal that allows entry into the nucleus by active transport through the nuclear pore (Bukrinsky, M. I. et al. 1993. Nature 365:666–669). Furthermore, the HIV vpr and vif accessory proteins contribute to transduction of some non-dividing cells (Connor, R. I. et al. 1995. Virology 206:935–944; Zufferey, R. D. et al. 1997. Nature Biotech. 15:871–875; Kafri, T. et al. 1997. Nature genetics 17:314–317). This distinctive property has been exploited to engineer vectors based on the HIV. These vectors can efficiently transduce non-dividing human hematopoietic stem cells (Evans, J. T. et al. 1999. Human Gene Therapy 10:1479–1489; Case, S. S. et al. 1999. Proc. Natl. Acad. Sci. USA 96:2988–2993; Uchida, N. et al. 1998. Proc. Natl. Acad. Sci. USA 95:11939–11944; Miyoshi, H. et al. 1999. Science 283:682–686; Sutton, R. E. et al. 1998. J. Virol. 72:5781–5788), and other cells such as neurons (Naldini, L. et al. 1996. Proc. Natl. Acad. Sci. USA 93:11382–11388), skeletal muscle (Kafri, T. et al. 1997. Nature Genetics 17:314–317), and hepatocytes (Kafri, T. et al. 1997. Nature Genetics 17:314–317).

One disadvantage of the HIV-based vectors has been the weak expression by the HIV LTR enhancer/promoter in hematopoietic cells. To compensate for this weakness, some HIV-based vectors express the HIV accessory protein tat that enhances transcription off the HIV LTR (Evans, J. T. et al. 1999. Human Gene Therapy 10:1479–1489; Case, S. S. et al. 1999. Proc. Natl. Acad. Sci. USA 96:2988–2993; Uchida, N. et al. 1998. Proc. Natl. Acad. Sci. USA 95:11939–11944). However, tat also enhances the expression of some cellular genes (Chirivi, R. G. et al. 1999. Blood 94:1747–1754; Weiss, J. M. et al. 1999. J. Immunol. 163:2953–2959; Barillari, G. et al. 1999. J. Immunol. 164:1929–1935; Demarchi, F. et al. 1999. J. Virol. 73:7080–7086; Maggirwar, S. B. et al. 1999. J. Neurochem. 73:578–586; Lefevre, E. A. et al. 1999. J. Immunol. 163:1119–1122) potentially disrupting the normal function of the transduced cell, although hematopoiesis in mice appears not to be grossly affected by over-expression of tat (Frazier, A. L. and J. V. Garcia. 1994. AIDS Res. Human Retrovir. 10:1517–1519). Furthermore, tat protein itself can enter cells (Schwarze, S. R. et al. 1999. Science 185:1569–1572) and thus may lead to tat expression in bystander non-target cells. Other HIV-based vectors use an internal CMV enhancer/promoter to drive the expression (Miyoshi, H. et al. 1999. Science 283:682–686). However, the expression in hematopoietic cells is low (Miyoshi, H. et al. 1999. Science 283:682–686), approximately 2 logs less than expression by the MuLV-based vector.

The recently described HIV-based lentiviral vector has been shown to be efficient in integrating into non-cycling cells (Verma, I. M. and N. Somia. 1997. Source Nature 389:239–30 242). Studies to determine the usefulness of this vector have been performed by Choi, J. K. and A. Gewirtz. (1998. Blood 92:468a). Using the enhanced green fluorescent protein (EGFP) as the reporter protein, it was found that the cellular expression of the lentivirus vector either from the HIV LTR promoter/enhancer or from an internal CMV promoter/enhancer was poor. FACS analysis of transduced hematopoietic cells demonstrated that EGFP fluorescent intensity in the lentiviral-transduced cells was only one-half log greater than control cells. This value negatively contrasted with the 2 to 3 log fluorescence signal augmentation observed in cells transduced with the MSCV-based system. To obtain better expression, Uchida et al. (1998. Proc. Natl. Acad. Sci. USA 95:11939–11944) successfully utilized a HIV-based vector system that also expressed the viral transcription co-factor tat that is critical for high expression off the HIV LTR. However, the uncharacterized physiological effect and immunological response of expression the viral tat protein is a problem for clinical safety.

Thus, the HIV-based vectors need further improvements.

A hybrid HIV/murine stem cell virus(MSCV) vector has now been developed wherein the original internal CMV enhancer/promoter is removed and the U3 region of the HIV LTR is partially replaced by the U3 region of the MSCV LTR. As demonstrated herein, this hybrid provides a safe vector with a high transduction efficiency. Thus, this new hybrid viral vector has advantages over previously available vectors.

SUMMARY OF THE INVENTION

An object of the present invention is to provide a hybrid viral vector which comprises a human immunodeficiency virus-based lentivirus and a murine stem cell retrovirus. In a preferred embodiment, this vector further comprises a selected gene for transduction via the viral vector into mammalian cells.

Another object of the present invention is to provide a method for transducing a selected gene into a cell which comprises administering to the cell a hybrid viral vector containing a human immunodeficiency virus-based lentivirus, a murine stem cell retrovirus and the selected gene.

Yet another object of the present invention is a method for delivering a selected gene to cells in a mammal which comprises administering to the mammal a hybrid viral vector containing a human immunodeficiency virus-based lentivirus, a murine stem cell retrovirus and the selected gene.

Figure 1:
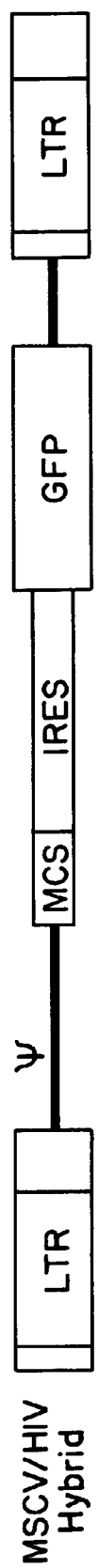
FIG. 1 is a diagram of a constructed hybrid retroviral vector of the present invention. In the FIG. "LTR" denotes long terminal repeats, "ψ" denotes viral packaging signal, "MCS" denotes multicloning site, "IRES" denotes internal ribosomal entry site, and "GFP" denotes green fluorescent protein.

The hybrid viral vector of the present invention was constructed using HIV vector pHR'CMVLacZ which was modified by replacing the original multicloning site (MCS) and LacZ with the MCS, internal ribosome entry site, and enhanced green fluorescent protein (EGFP) from the bicistronic MSCV based vector M1GR1. The resulting vector pHR'CMV-IRES-GFP was further modified by deleting the internal CMV enhancer/promoter and replacing the 3'HIV LTR with a hybrid HIV/MSCV LTR. To generate the hybrid LTR, 50 bp of the 5' end of the HIV U3 region, the complete MSCV LTR, and the 50 bp of the 3' end of the HIV U3 region followed by the complete HIV RU5 region were individually amplified by PCR using primers listed in Table 1. The resulting 3 fragments were joined together by extension PCR and the resulting hybrid HIV/MSCV LTR was amplified by PCR using the primers HIV-U3 5'A (SEQ ID NO:1) and HIV-RU5 3'A (SEQ ID NO:6).

TABLE 1

Oligonucleotides Used to Generate the HIV/MSCV LTR

| Oligonucleotide Name | Sequence | |
|---|---|---|
| HIV-U3 5'A | ccgctcgagacctggaaaaacatg | (SEQ ID NO:1) |
| HIV-U3 3'A | aggtggggtctttcaatccacagatcaaggatatc | (SEQ ID NO:2) |
| MSCV-LTR 3'C | tgagggctcgccactacgggtacccgggcgacgca | (SEQ ID NO:3) |
| MSCV-LTR 5'C | tgaaagacccacctgtagg | (SEQ ID NO:4) |
| HIV-RU5 3'B | agtggcgagccctcagatgc | (SEQ ID NO:5) |
| HIV-RU5 3'A | ggactagtgaagcactcaaggcaagct | (SEQ ID NO:6) |

DETAILED DESCRIPTION OF THE INVENTION

A hybrid viral vector has now been developed which exhibits high expression of an exogenous gene in non-dividing cells and which does not possess the potential hazards associated with use of the viral tat protein. The vector of the present invention is a HIV lentivirus/murine stem cell virus hybrid vector. More specifically, in the hybrid viral vector of the present invention an internal CMV enhancer/promoter of the HIV lentiviral vector is removed and a U3 region of a 3' HIV LTR of the HIV lentiviral vector is partially replaced by a U3 region of a 3' murine stem cell virus LTR (See FIG. 1). "Partially replaced" in the present invention is defined as replacement with a hybrid LTR that comprises approximately 50 bp of the 5' end of the HIV U3 region, the complete MSCV LTR, and approximately 50 bp of the 3' end of the HIV U3 region followed by the complete HIV RU5 region.

High gene expression has now been demonstrated using this hybrid viral vector. In these experiments, viral particles were generated via the vector in 293T cells using transient transfection with VSV-G pseudotyping. The viral particles were then used to transduce dividing and non-dividing human hematopoietic cells. For these experiments, the hybrid viral vector also comprised the exogenous gene encoding green fluorescent protein (GFP). FACS analysis of the transduced cells demonstrated a significant increase in the expression of the hybrid LTR resulting in a fluorescent signal 1.5 to 2 logs greater than the control cells transduced with an HIV-based vector containing the internal CMV enhancer/promoter. Thus, the hybrid viral vector of the present invention exhibits the high transduction efficiency of the HIV-based vector and the high expression of the MuLV-based vector even in non-dividing stem cells.

The packaging plasmid CMVdeltaR8.2 and the VSV-G envelope plasmid PMD.G were used. Once produced, the viral vector was characterized in cells in culture using hematopoietic precursor cells and FACS analysis.

The hybrid viral vector of the present invention is useful for transfer of selected genes into hematopoietic stem cells as well as other non-dividing cells including, but not limited to, cells of the skin, gastrointestinal tissue, cardiac tissue, and neuronal tissue. Techniques for transfer of selected genes into tissue or cells using viral vectors is well-established in the art. Further genes for selection and transfer via viral vectors are well known. One of skill can thus use these established techniques with the hybrid viral vector of the present invention to efficiently transfer selected genes to cells and mammals. The characteristics of high expression and safety make the hybrid viral vector of the present invention a desirable vector for gene transfer to both cells and mammals. In a preferred embodiment, the viral vector of the present invention is administered to a mammal, preferably a human. The vectors can be administered orally or parenterally, including intravenously, intramuscularly, intraperitoneally, intranasally, subcutaneously, or surgically. When administered parenterally, it is preferred that the vectors be given in a pharmaceutical vehicle suitable for injection such as a sterile aqueous solution or dispersion. Following administration, the mammal is monitored to detect changes in gene expression. Dose and duration of treatment is determined individually depending on the condition or disease to be treated. A wide variety of conditions or diseases can be treated based on the gene expression produced by administration of the gene of interest in the vector of the present invention.

The following nonlimiting examples are provided to further illustrate the present invention.

EXAMPLES

Example 1

Generation of Virus

MSCV-Based Retrovirus: Retroviruses were generated using standard methods such as those described by Pear, W. S. et al. (1998. *Blood* 92:3780–3792). In this method M1GR1 and a vector that encodes the viral envelope protein VSV-G were transiently co-transfected into the packaging cell line GP that provides the retroviral gag-pol proteins. During the next three days, the transfected GP cells release retroviruses into the culture medium; each ml of media contains $10^5$ to $10^6$ infectious viral particles. The culture media were collected 48 and 72 hours post transfection and stored in small aliquots at $-70°$ C.

HIV based lentivirus: Lentiviral particles were generated in 293T cells using transient transfection with plasmids encoding the RNA genome, viral protein, and VSV-G envelope protein following standard methods (Naldini, L. et al. 1996. *Proc. Natl. Acad. Sci.* 93:11382–11388). Viral particles were collected and stored as described for the MSCV-based retrovirus.

The titer of the virus was determined by transducing the hematopoietic cell line K562. For transduction, 2–4 million cells, 1 ml of the harvested culture media, and 8 micrograms per milliliter of polybrene was centrifuged in a 24 well plate at 1500×g for 90 minutes. Afterwards, the cells were transferred to fresh media.

Example 2

Tissue Culture

K562 cells were cultured in RPMI supplemented with 10% fetal bovine serum. 293T cells and GP cells were cultured in DMEM supplemented with 10% fetal bovine serum. Primary human hematopoietic cells from bone marrow aspirates or umbilical cord blood were purified by Ficoll gradient followed by positive immuno-magnetic selection for CD34. CD34+ cells were cultured in IMDM supplemented with 12.5% horse serum and 12.5% fetal bovine serum. In some experiments the media were further supplemented with the growth factors stem cell factor, thrombopoietin, and flk-3.

Primary CD34+ bone marrow or umbilical cord blood cells were transduced and cultured on a monolayer of primary bone marrow stromal cells for 5 weeks. Cells were trypsinized and plated into methylcellulose cultures with IL-3 and GM-CSF. Colonies were evaluated 10–12 days later under phase and uv microscopy.

---

What is claimed is:

1. A hybrid viral vector comprising a human immunodeficiency virus and a murine stem cell retrovirus wherein the 3' long terminal repeat of said lentivirus is replaced by a modified 3' long terminal repeat comprising 50 base pairs of a 5', end of the human immunodeficiency virus U3 region, a complete murine stem cell retrovirus long terminal repeat, and 50 base pairs of a 3' end of the human immunodeficiency virus U3 region followed by a complete human immunodeficiency virus RU5 region, operably linked in that order.

2. The hybrid viral vector of claim 1 further comprising a selected gene operatively linked to said modified 3' long terminal repeat.

3. A method of transducing cells with a selected gene comprising administering to the cells in vitro the hybrid viral vector of claim 2.

* * * * *

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 1
ccgctcgaga cctggaaaaa catg                                           24

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 2
aggtggggtc tttcaatcca cagatcaagg atatc                               35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 3
tgagggctcg ccactacggg tacccgggcg acgca                               35

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic

```
<400> SEQUENCE: 4
tgaaagaccc cacctgtagg                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:  Synthetic

<400> SEQUENCE: 5
agtggcgagc cctcagatgc                                                    20

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:  Synthetic

<400> SEQUENCE: 6
ggactagtga agcactcaag gcaagct                                            27
```